(12) United States Patent
Harichian et al.

(10) Patent No.: US 8,124,063 B2
(45) Date of Patent: *Feb. 28, 2012

(54) METHOD FOR MOISTURIZING HUMAN SKIN USING DIHYDROXYPROPYLTRI($C_1$-$C_3$ ALKYL) AMMONIUM SALTS

(75) Inventors: Bijan Harichian, Warren, NJ (US); Richard Loren McManus, Shelton, CT (US); Jose Guillermo Rosa, Edgewater, NJ (US)

(73) Assignee: Conopco, Inc., Englewood Cliffs, NJ (US)

( * ) Notice: Subject to any disclaimer, the term of this patent is extended or adjusted under 35 U.S.C. 154(b) by 1544 days.

This patent is subject to a terminal disclaimer.

(21) Appl. No.: 10/972,483

(22) Filed: Oct. 25, 2004

(65) Prior Publication Data

US 2006/0088495 A1 Apr. 27, 2006

(51) Int. Cl.
*A61K 31/74* (2006.01)
(52) U.S. Cl. .................. 424/78.02; 424/78.03
(58) Field of Classification Search ............... 424/78.02, 424/78.03
See application file for complete search history.

(56) References Cited

U.S. PATENT DOCUMENTS

| | | | | |
|---|---|---|---|---|
| 4,114,632 A * | 9/1978 | Morganroth | ............... | 132/208 |
| 4,663,159 A | 5/1987 | Brode, II et al. | | |
| 4,689,217 A | 8/1987 | Restaino et al. | | |
| 4,690,817 A | 9/1987 | Davis et al. | | |
| 4,740,367 A * | 4/1988 | Force et al. | ............... | 424/47 |
| 4,758,599 A * | 7/1988 | Minetti | ............... | 514/355 |
| 4,775,715 A | 10/1988 | Beresniewicz et al. | | |
| 4,919,838 A * | 4/1990 | Tibbetts et al. | ............... | 510/120 |
| 4,978,526 A * | 12/1990 | Gesslein et al. | ............... | 424/70.28 |
| 5,156,837 A * | 10/1992 | Chaudhuri et al. | ............... | 424/70.28 |
| 5,463,127 A * | 10/1995 | Deavenport et al. | ............... | 564/292 |
| 5,552,137 A * | 9/1996 | Manning et al. | ............... | 424/70.1 |
| 5,698,183 A | 12/1997 | Langer et al. | | |
| 6,020,422 A * | 2/2000 | Connors et al. | ............... | 524/716 |
| 6,120,554 A * | 9/2000 | Patton et al. | ............... | 8/102 |
| 6,290,978 B2 | 9/2001 | Mak et al. | | |
| 6,649,177 B2 | 11/2003 | Howard et al. | | |
| 6,869,977 B1 * | 3/2005 | O'Lenick et al. | ............... | 564/291 |
| 7,087,560 B2 * | 8/2006 | McManus et al. | ............... | 510/119 |
| 7,176,172 B2 * | 2/2007 | Harding et al. | ............... | 510/130 |
| 7,226,900 B2 * | 6/2007 | Delplancke et al. | ............... | 510/470 |
| 7,282,471 B2 * | 10/2007 | Harichian et al. | ............... | 510/130 |
| 2003/0206933 A1 | 11/2003 | Schulze zur Wiesche et al. | | |
| 2003/0211952 A1 | 11/2003 | Erazo-Majewicz et al. | | |
| 2004/0110651 A1 * | 6/2004 | Harmalker et al. | ............... | 510/130 |
| 2004/0156877 A1 | 8/2004 | Tokuyama et al. | | |

FOREIGN PATENT DOCUMENTS

| | | |
|---|---|---|
| EP | 1 179 339 | 2/2002 |
| EP | 1 366 742 | 12/2003 |
| JP | 01019051 A * | 7/1987 |
| JP | 63068514 | 3/1988 |
| JP | 1249709 | 10/1989 |
| JP | 9012589 | 1/1997 |
| WO | WO 96/35410 | 11/1996 |
| WO | 00/61066 | 10/2000 |

OTHER PUBLICATIONS

Lieb et al. "A new in vitro method for transepidermal water loss: A possible method for moisturizer evaluation"; J. Soc. cosmet. Chem., 39, 107-119 (Mar./Apr. 1988.*
Dow—Quat 188 Cationic Monomer: Overview, Jun. 30, 2004.
Arch Personal Care Products Brochure—Honeyquat 50 Substantive Honey Derivative, Jan. 2004.
Arch Personal Care Products—In vivo study of moisturizing effects of HoneyQuat 50, Jan. 2004.

* cited by examiner

*Primary Examiner* — Isis Ghali
(74) *Attorney, Agent, or Firm* — Milton L. Honig

(57) ABSTRACT

A personal care product is provided which includes a composition containing dihydroxypropyltri($C_1$-$C_3$ alkyl)ammonium salt in a carrier. The composition is packaged for delivery to a consumer and includes instructions printed on or associated with the packaging indicating topical use of the composition on skin, hair or the oral mucosae. Particularly useful is dihydroxypropyltrimonium chloride which operates as a humectant to moisturize both at high and low relative humidity environments.

7 Claims, No Drawings

METHOD FOR MOISTURIZING HUMAN SKIN USING DIHYDROXYPROPYLTRI($C_1$-$C_3$ ALKYL) AMMONIUM SALTS

BACKGROUND OF THE INVENTION

1. Field of the Invention

The invention concerns personal care compositions providing moisturization both in high and low relative humidity environments.

2. The Related Art

Dry skin is a problem in varying degree to most humans. This condition is particularly evident in winter. Personal care products such as skin creams/lotions, shampoos/conditioners, toilette bars/shower gels and antiperspirant/deodorants are normally formulated with at least one material to address dry skin. Symptoms such as itching, flaking and a visually displeasing dermal appearance can all to some extent be modulated.

There are three classes of materials employed against the problem. Occlusives such as petrolatum or silicone oils serve to inhibit loss of natural moisture. They form a barrier between the epidermis and the environment. Another approach is the use of keratolytic agents to enhance rate of dermal exfoliation. Alpha-hydroxy acids are the most common agents for achieving exfoliation.

A third approach to dry skin is topical application of humectants. Hydroxylated monomeric and polymeric organic substances are generally used for this purpose. Glycerin known also as glycerol is one of the most effective humectants.

There are several shortcomings in the performance of known humectants. Even the best such as glycerin requires to be formulated at relatively high levels to achieve good moisturization. Secondly, known humectants perform well in high relative humidity environments; however, hardly any of these substances provide effectiveness at low relative humidity (i.e. less than 20% moisture at 20° C.). Average indoor relative humidity during winter is approximately 13% in areas such as the Northeast U.S. It is quite evident that a real need exists for an improved moisturization technology.

A moisturizer known as Honeyquat 50 with INCI name of Hydroxypropyltrimonium Honey has been reported to be a better humectant than glycerin. See the Arch/Brooks brochure titled "Cosmetic Ingredients & Ideas®", Issue No. 2, August 2001. Honeyquat 50 is described as being derived from the reaction of pendent hydroxyl groups (on the disaccharide) of a "light" deodorized grade of honey with a chlorohydroxytrimethylammonium derivative. Although this substance has excellent humectancy, moisturization at low relative humidity still remains to be conquered.

Accordingly, the present invention seeks to identify humectants which are operative not only at high but also low relative humidity, for application in personal care products.

SUMMARY OF THE INVENTION

A personal care product is provided which includes:
(A) a personal care composition including:
   (i) from about 0.1 to about 30% by weight of dihydroxypropyltri($C_1$-$C_3$ alkyl) ammonium salt;
   (ii) a cosmetically acceptable carrier;
(B) a package for delivering the composition to a consumer; and
(C) instructions printed on or associated with the package indicating topical use of the composition on skin.

DETAILED DESCRIPTION OF THE INVENTION

Now it has been found that hydroxypropyltri($C_1$-$C_3$ alkyl) ammonium salts are excellent moisturizers providing humectancy at both high and low relative humidity environments. These salts may be obtained in a variety of synthetic procedures, most particularly by hydrolysis of chlorohydroxypropyltri($C_1$-$C_3$ alkyl)ammonium salts. A most preferred species is 1,2-dihydroxypropyltrimonium chloride, wherein the $C_1$-$C_3$ alkyl is a methyl group. Amounts of the salt may range from about 0.1 to about 30%, preferably from about 0.5 to about 20%, optimally from about 1% to about 12% by weight of the composition.

Ordinarily the $C_1$-$C_3$ alkyl constituent on the quaternized ammonium group will be methyl, ethyl, n-propyl, isopropyl or hydroxyethyl and mixtures thereof. Particularly preferred is a trimethyl ammonium group known through INCI nomenclature as a "trimonium" group. Any anion can be used in the quat salt. The anion may be organic or inorganic with proviso that the material is cosmetically acceptable. Typical inorganic anions are halides, sulfates, phosphates, nitrates and borates. Most preferred are the halides, especially chloride. Organic anionic counter ions include methosulfate, toluoyl sulfate, acetate, citrate, tartrate, lactate, gluconate, and benzenesulfonate.

By the term personal care composition is meant any substance applied to a human body for improving appearance, cleansing, odor control or general aesthetics. Nonlimiting examples of personal care compositions include leave-on skin lotions and creams, shampoos, hair conditioners, shower gels, toilet bars, antiperspirants, deodorants, dental products, shave creams, depilatories, lipsticks, foundations, mascara, sunless tanners and sunscreen lotions.

Compositions of this invention will also include a cosmetically acceptable carrier. Amounts of the carrier may range from about 1 to about 99.9%, preferably from about 70 to about 95%, optimally from about 80 to about 90% by weight of the composition. Among the useful carriers are water, emollients, fatty acids, fatty alcohols, thickeners and combinations thereof. The carrier may be aqueous, anhydrous or an emulsion. Preferably the compositions are aqueous, especially water and oil emulsions of the W/O or O/W or triplex W/O/W variety. Water when present may be in amounts ranging from about 5 to about 95%, preferably from about 20 to about 70%, optimally from about 35 to about 60% by weight.

Emollient materials may serve as cosmetically acceptable carriers. These may be in the form of silicone oils, natural or synthetic esters and hydrocarbons. Amounts of the emollients may range anywhere from about 0.1 to about 95%, preferably between about 1 and about 50% by weight of the composition.

Silicone oils may be divided into the volatile and nonvolatile variety. The term "volatile" as used herein refers to those materials which have a measurable vapor pressure at ambient temperature. Volatile silicone oils are preferably chosen from cyclic (cyclomethicone) or linear polydimethylsiloxanes containing from 3 to 9, preferably from 4 to 5, silicon atoms.

Nonvolatile silicone oils useful as an emollient material include polyalkyl siloxanes, polyalkylaryl siloxanes and polyether siloxane copolymers. The essentially nonvolatile polyalkyl siloxanes useful herein include, for example, polydimethyl siloxanes with viscosities of from about $5 \times 10^{-6}$ to 0.1 $m^2$/s at 25° C. Among the preferred nonvolatile emollients useful in the present compositions are the polydimethyl siloxanes having viscosities from about $1\times10^{-5}$ to about $4\times10^{-4}$ m$^2$/s at 25° C.

Another class of nonvolatile silicones are emulsifying and non-emulsifying silicone elastomers. Representative of this category is Dimethicone/Vinyl Dimethicone Crosspolymer available as Dow Corning 9040, General Electric SFE 839, and Shin-Etsu KSG-18. Silicone waxes such as Silwax WS-L (Dimethicone Copolyol Laurate) may also be useful.

Among the ester emollients are:

a) Alkyl esters of saturated fatty acids having 10 to 24 carbon atoms. Examples thereof include behenyl neopentanoate, isononyl isonanonoate, isopropyl myristate and octyl stearate.

b) Ether-esters such as fatty acid esters of ethoxylated saturated fatty alcohols.

c) Polyhydric alcohol esters. Ethylene glycol mono- and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 monostearate, ethoxylated propylene glycol monostearate, glyceryl mono- and di-fatty acid esters, polyglycerol poly-fatty esters, ethoxylated glyceryl mono-stearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters. Particularly useful are pentaerythritol, trimethylolpropane and neopentyl glycol esters of $C_1$-$C_{30}$ alcohols.

d) Wax esters such as beeswax, spermaceti wax and tribehenin wax.

e) Sugar ester of fatty acids such as sucrose polybehenate and sucrose polycottonseedate.

Natural ester emollients principally are based upon mono-, di- and tri-glycerides. Representative glycerides include sunflower seed oil, cottonseed oil, borage oil, borage seed oil, primrose oil, castor and hydrogenated castor oils, rice bran oil, soybean oil, olive oil, safflower oil, shea butter, jojoba oil and combinations thereof. Animal derived emollients are represented by lanolin oil and lanolin derivatives. Amounts of the natural esters may range from about 0.1 to about 20% by weight of the compositions.

Hydrocarbons which are suitable cosmetically acceptable carriers include petrolatum, mineral oil, $C_{11}$-$C_{13}$ isoparaffins, polybutenes, and especially isohexadecane, available commercially as Permethyl 101A from Presperse Inc.

Fatty acids having from 10 to 30 carbon atoms may also be suitable as cosmetically acceptable carriers. Illustrative of this category are pelargonic, lauric, myristic, palmitic, stearic, isostearic, oleic, linoleic, linolenic, hydroxystearic and behenic acids.

Fatty alcohols having from 10 to 30 carbon atoms are another useful category of cosmetically acceptable carrier. Illustrative of this category are stearyl alcohol, lauryl alcohol, myristyl alcohol, oleyl alcohol and cetyl alcohol.

Thickeners can be utilized as part of the cosmetically acceptable carrier of compositions according to the present invention. Typical thickeners include crosslinked acrylates (e.g. Carbopol 982®), hydrophobically-modified acrylates (e.g. Carbopol 1382®), polyacrylamides (e.g. Sepigel 305®), acryloylmethylpropane sulfonic acid/salt polymers and copolymers (e.g. Aristoflex HMB® and AVC®), cellulosic derivatives and natural gums. Among useful cellulosic derivatives are sodium carboxymethylcellulose, hydroxypropyl methocellulose, hydroxypropyl cellulose, hydroxyethyl cellulose, ethyl cellulose and hydroxymethyl cellulose. Natural gums suitable for the present invention include guar, xanthan, sclerotium, carrageenan, pectin and combinations of these gums. Inorganics may also be utilized as thickeners, particularly clays such as bentonites and hectorites, fumed silicas, talc, calcium carbonate and silicates such as magnesium aluminum silicate (Veegum®). Amounts of the thickener may range from 0.0001 to 10%, usually from 0.001 to 1%, optimally from 0.01 to 0.5% by weight of the composition.

Adjunct humectants may be employed in the present invention. These are generally polyhydric alcohol-type materials. Typical polyhydric alcohols include glycerol, propylene glycol, dipropylene glycol, polypropylene glycol, polyethylene glycol, sorbitol, hydroxypropyl sorbitol, hexylene glycol, 1,3-butylene glycol, isoprene glycol, 1,2,6-hexanetriol, ethoxylated glycerol, propoxylated glycerol and mixtures thereof. The amount of adjunct humectant may range anywhere from 0.5 to 50%, preferably between 1 and 15% by weight of the composition.

Personal care compositions of the present invention may be in any form. These forms may include lotions, creams, roll-on formulations, sticks, mousses, aerosol and non-aerosol sprays and fabric (e.g. nonwoven textile)-applied formulations.

Surfactants may also be present in compositions of the present invention. Total concentration of the surfactant when present may range from about 0.1 to about 90%, preferably from about 1 to about 40%, optimally from about 1 to about 20% by weight of the composition, and being highly dependent upon the type of personal care product. The surfactant may be selected from the group consisting of anionic, nonionic, cationic and amphoteric actives. Particularly preferred nonionic surfactants are those with a $C_{10}$-$C_{20}$ fatty alcohol or acid hydrophobe condensed with from 2 to 100 moles of ethylene oxide or propylene oxide per mole of hydrophobe; $C_2$-$C_{10}$ alkyl phenols condensed with from 2 to 20 moles of alkylene oxide; mono- and di-fatty acid esters of ethylene glycol; fatty acid monoglyceride; sorbitan, mono- and di-$C_8$-$C_{20}$ fatty acids; and polyoxyethylene sorbitan as well as combinations thereof. Alkyl polyglycosides and saccharide fatty amides (e.g. methyl gluconamides) and trialkylamine oxides are also suitable nonionic surfactants.

Preferred anionic surfactants include soap, alkyl ether sulfates and sulfonates, alkyl sulfates and sulfonates, alkylbenzene sulfonates, alkyl and dialkyl sulfosuccinates, $C_8$-$C_{20}$ acyl isethionates, $C_8$-$C_{20}$ alkyl ether phosphates, $C_8$-$C_{20}$ sarcosinates, $C_8$-$C_{20}$ acyl lactylates, sulfoacetates and combinations thereof.

Useful amphoteric surfactants include cocoamidopropyl betaine, $C_{12}$-$C_{20}$ trialkyl betaines, sodium lauroamphoacetate, and sodium laurodiamphoacetate.

Sunscreen agents may also be included in compositions of the present invention. Particularly preferred are such materials as ethylhexyl p-methoxycinnamate, available as Parsol MCX®, Avobenzene, available as Parsol 1789® and benzophenone-3, also known as Oxybenzone. Inorganic sunscreen actives may be employed such as microfine titanium dioxide and zinc oxide. Amounts of the sunscreen agents when present may generally range from 0.1 to 30%, preferably from 2 to 20%, optimally from 4 to 10% by weight of the composition.

Antiperspirants and deodorant compositions of the present invention ordinarily will contain astringent actives. Examples include aluminum chloride, aluminum chlorhydrex, aluminim-zirconium chlorhydrex glycine, aluminum sulfate, zinc sulfate, zirconium and aluminum chlorohydroglycinate, zirconium hydroxychloride, zirconium and aluminum lactate, zinc phenolsulfonate and combinations thereof.

Amounts of the astringents may range anywhere from about 0.5 to about 50% by weight of the composition.

Dental products formulated according to the present invention will generally contain a fluoride source to prevent dental caries. Typical anti-caries actives include sodium fluoride, stannous fluoride and sodium monofluoro phosphate. Amounts of these materials will be determined by the amount of fluoride releasable which should range between about 500 to about 8800 ppm of the composition. Other components of dentifrices can include desensitizing agents such as potassium nitrate and strontium nitrate, sweeteners such as sodium saccharine, aspartame, sucralose, and potassium acesulfam. Thickeners, opacifying agents, abrasives and colorants will normally also be present.

Preservatives can desirably be incorporated into the personal care compositions of this invention to protect against the growth of potentially harmful microorganisms. Particularly preferred preservatives are phenoxyethanol, methyl paraben, propyl paraben, imidazolidinyl urea, dimethyloldimethylhydantoin, ethylenediaminetetraacetic acid salts (EDTA), sodium dehydroacetate, methylchloroisothiazolinone, methylisothiazolinone, iodopropynbutylcarbamate and benzyl alcohol. The preservatives should be selected having regard for the use of the composition and possible incompatibilities between the preservatives and other ingredients. Preservatives are preferably employed in amounts ranging from 0.0001% to 2% by weight of the composition.

Compositions of the present invention may include vitamins. Illustrative vitamins are Vitamin A (retinol), Vitamin $B_2$, Vitamin $B_3$ (niacinamide), Vitamin $B_6$, Vitamin C, Vitamin E, Folic Acid and Biotin. Derivatives of the vitamins may also be employed. For instance, Vitamin C derivatives include ascorbyl tetraisopalmitate, magnesium ascorbyl phosphate and ascorbyl glycoside. Derivatives of Vitamin E include tocopheryl acetate, tocopheryl palmitate and tocopheryl linoleate. DL-panthenol and derivatives may also be employed. For purposes of this invention, vitamins where present are not considered as unsaturated materials. Total amount of vitamins when present in compositions according to the present invention may range from 0.001 to 10%, preferably from 0.01% to 1%, optimally from 0.1 to 0.5% by weight of the composition.

Another type of useful substance can be that of an enzyme such as amylases, oxidases, proteases, lipases and combinations. Particularly preferred is superoxide dismutase, commercially available as Biocell SOD from the Brooks Company, USA.

Skin lightening compounds may be included in the compositions of the invention. Illustrative substances are placental extract, lactic acid, niacinamide, arbutin, kojic acid, ferulic acid, resorcinol and derivatives including 4-substituted resorcinols and combinations thereof. Amounts of these agents may range from about 0.1 to about 10%, preferably from about 0.5 to about 2% by weight of the composition.

Desquamation promoters may be present. Illustrative are the alpha-hydroxycarboxylic acids and beta-hydroxycarboxylic acids. The term "acid" is meant to include not only the free acid but also salts and $C_1$-$C_{30}$ alkyl or aryl esters thereof and lactones generated from removal of water to form cyclic or linear lactone structures. Representative acids are glycolic, lactic and malic acids. Salicylic acid is representative of the beta-hydroxycarboxylic acids. Amounts of these materials when present may range from about 0.01 to about 15% by weight of the composition.

A variety of herbal extracts may optionally be included in compositions of this invention. The extracts may either be water soluble or water-insoluble carried in a solvent which respectively is hydrophilic or hydrophobic. Water and ethanol are the preferred extract solvents. Illustrative extracts include those from green tea, chamomile, licorice, aloe vera, grape seed, citrus unshui, willow bark, sage, thyme and rosemary.

Also included may be such materials as lipoic acid, retinoxytrimethylsilane (available from Clariant Corp. under the Silcare 1M-75 trademark), dehydroepiandrosterone (DHEA) and combinations thereof. Ceramides (including Ceramide 1, Ceramide 3, Ceramide 3B and Ceramide 6) as well as pseudoceramides may also be useful. Amounts of these materials may range from about 0.000001 to about 10%, preferably from about 0.0001 to about 1% by weight of the composition.

Colorants, opacifiers and abrasives may also be included in compositions of the present invention. Each of these substances may range from about 0.05 to about 5%, preferably between 0.1 and 3% by weight of the composition.

The compositions of the present invention can also be, optionally, incorporated into an insoluble substrate for application to the skin such as in the form of a treated wipe.

A wide variety of packaging can be employed to store and deliver the personal care compositions. Packaging is often dependent upon the type of personal care end-use. For instance, leave-on skin lotions and creams, shampoos, hair conditioners and shower gels generally employ plastic containers with an opening at a dispensing end covered by a closure. Typical closures are screw-caps, non-aerosol pumps and flip-top hinged lids. Packaging for antiperspirants, deodorants and depilatories may involve a container with a roll-on ball on a dispensing end. Alternatively these types of personal care products may be delivered as a stick composition formulation in a container with propel-repel mechanism where the stick moves on a platform towards a dispensing orifice. Metallic cans pressurized by a propellant and having a spray nozzle serve as packaging for antiperspirants, shave creams and other sprayable personal care products. Toilette bars may have packaging constituted by a cellulosic or plastic wrapper or within a cardboard box or even encompassed by a shrink wrap plastic film. All of the aforementioned are considered packaging within the context of the present invention.

Another aspect of personal care products of this invention will be the inclusion of instructions attached to or otherwise associated with the packaging. The instructions indicate to a consumer topical use of the composition on skin, hair or oral mucosae. Packaging itself will usually be printed with the instructions but sometimes a separate written insert within the package may serve to provide the instructions. Typical language includes phrases such as "apply a thin layer to the underarm", "apply regularly to hands", "apply to wet hair, lather and rinse", "cleanse skin" and "pump a small amount onto the palm of your hand".

The term "comprising" is meant not to be limiting to any subsequently stated elements but rather to encompass non-specified elements of major or minor functional importance. In other words the listed steps, elements or options need not be exhaustive. Whenever the words "including" or "having" are used, these terms are meant to be equivalent to "comprising" as defined above.

Except in the operating and comparative examples, or where otherwise explicitly indicated, all numbers in this description indicating amounts of material ought to be understood as modified by the word "about".

All documents referred to herein, including all patents, patent applications, and printed publications, are hereby incorporated by reference in their entirety in this disclosure.

The following examples will more fully illustrate the embodiments of this invention. All parts, percentages and proportions referred to herein and in the appended claims are by weight unless otherwise illustrated.

Example 1

A representative personal care composition of the present invention in the form of a cosmetic lotion is outlined under Table I.

TABLE I

| INGREDIENT | WEIGHT % |
|---|---|
| PHASE A | |
| Water | Balance |
| Disodium EDTA | 0.05 |
| Methyl Paraben | 0.15 |
| Magnesium Aluminum Silicate | 0.60 |
| Triethanolamine | 1.20 |
| Dihydroxypropytrimonium Chloride | 1.00 |
| PHASE B | |
| Xanthan Gum | 0.20 |
| Natrosol ® 250HHR (ethyl cellulose) | 0.50 |
| Butylene Glycol | 3.00 |
| Glycerin | 2.00 |
| PHASE C | |
| Sodium Stearoyl Lactylate | 0.10 |
| Glycerol Monostearate | 1.50 |
| Stearyl Alcohol | 1.50 |
| Isostearyl Palmitate | 3.00 |
| Silicone Fluid | 1.00 |
| Cholesterol | 0.25 |
| Sorbitan Stearate | 1.00 |
| Butylated Hydroxy Toluene | 0.05 |
| Vitamin E Acetate | 0.01 |
| PEG-100 Stearate | 2.00 |
| Stearic Acid | 3.00 |
| Propyl Paraben | 0.10 |
| Parsol MCX ® | 2.00 |
| Caprylic/Capric Triglyceride | 0.50 |
| Hydroxycaprylic Acid | 0.01 |
| C12-15 Alkyl Octanoate | 3.00 |
| PHASE D | |
| Vitamin A Palmitate | 0.10 |
| Bisabolol | 0.01 |
| Vitamin A Acetate | 0.01 |
| Fragrance | 0.03 |
| Retinol 50C | 0.02 |
| Conjugated Linoleic Acid | 0.50 |

Example 2

A water-in-oil topical liquid make-up foundation according to invention is described in Table II below.

TABLE II

| INGREDIENT | WEIGHT % |
|---|---|
| PHASE A | |
| Cyclomethicone | 9.25 |
| Oleyl Oleate | 2.00 |
| Dimethicone Copolyol | 20.00 |
| PHASE B | |
| Talc | 3.38 |
| Pigment (Iron Oxides) | 10.51 |
| Spheron L-1500 (Silica) | 0.50 |
| PHASE C | |
| Synthetic Wax Durachem 0602 | 0.10 |
| Arachidyl Behenate | 0.30 |
| PHASE D | |
| Cyclomethicone | 1.00 |
| Trihydroxystearin | 0.30 |
| PHASE E | |
| Laureth-7 | 0.50 |
| Propyl Paraben | 0.25 |
| PHASE F | |
| Fragrance | 0.05 |
| PHASE G | |
| Water | balance |
| Dihydroxypropytrimonium Chloride | 3.00 |
| Methyl Paraben | 0.12 |
| Propylene Glycol | 8.00 |
| Niacinamide | 4.00 |
| Glycerin | 3.00 |
| Sodium Chloride | 2.00 |
| Sodium Dehydroacetate | 0.30 |

Example 3

Illustrated herein is a skin cream incorporating a quat salt of the present invention.

TABLE III

| INGREDIENT | WEIGHT % |
|---|---|
| Glycerin | 6.93 |
| Niacinamide | 5.00 |
| Dihydroxypropytrimonium Chloride | 5.00 |
| Permethyl 101A[1] | 3.00 |
| Sepigel 305[2] | 2.50 |
| Q2-1403[3] | 2.00 |
| Linseed Oil | 1.33 |
| Arlatone 2121[4] | 1.00 |
| Cetyl Alcohol CO-1695 | 0.72 |
| SEFA Cottonate[5] | 0.67 |
| Tocopherol Acetate | 0.50 |
| Panthenol | 0.50 |
| Stearyl Alcohol | 0.48 |
| Titanium Dioxide | 0.40 |
| Disodium EDTA | 0.10 |
| Glydant Plus[6] | 0.10 |
| PEG-100 Stearate | 0.10 |
| Stearic Acid | 0.10 |
| Purified Water | Balance |

[1]Isohexadecane, Presperse Inc., South Plainfield, NJ
[2]Polyacrylamide(and)C13-14 Isoparaffin(and) Laureth-7, Seppic Corporation, Fairfield, NJ
[3]dimethicone(and)dimethiconol, Dow Corning Corp. Midland, MI
[4]Sorbitan Monostearate and Sucrococoate, ICI Americas Inc., Wilmington, DE
[5]Sucrose ester of fatty acid
[6]DMDM Hydantoin (and) Iodopropynyl Butylcarbamate, Lonza Inc., Fairlawn, NJ

Example 4

Illustrative of another cosmetic composition incorporating a quat salt according to the present invention is the formula of Table IV.

TABLE IV

| INGREDIENT | WEIGHT % |
|---|---|
| Polysilicone-11 | 29 |
| Cyclomethicone | 59 |
| Petrolatum | 11 |
| Dihydroxypropytrimonium Chloride | 0.2 |

TABLE IV-continued

| INGREDIENT | WEIGHT % |
|---|---|
| Dimethicone Copolyol | 0.5 |
| Sunflowerseed Oil | 0.3 |

Example 5

A relatively anhydrous composition and incorporating a quat salt of the present invention is reported in Table V.

TABLE V

| INGREDIENT | WEIGHT % |
|---|---|
| Cyclomethicone | 80.65 |
| Dimethicone | 9.60 |
| Squalane | 6.00 |
| Isostearic Acid | 1.90 |
| Borage Seed Oil | 0.90 |
| Dihydroxypropytrimonium Chloride | 0.50 |
| Retinyl Palmitate | 0.25 |
| Ceramide 6 | 0.10 |
| Tocopherol | 0.10 |

Example 6

An aerosol packaged foaming cleanser with a quat salt suitable for the present invention is outlined in Table VI.

TABLE VI

| INGREDIENT | WEIGHT % |
|---|---|
| Sunflower Seed Oil | 20.00 |
| Maleated Soybean Oil | 5.00 |
| Silicone Urethane | 1.00 |
| Polyglycero-4 Oleate | 1.00 |
| Sodium C14-16 Olefin Sulfonate | 15.00 |
| Sodium Lauryl Ether Sulphate (25% active) | 15.00 |
| Cocoamidopropylbetaine | 15.00 |
| DC 1784 ® (Silicone Emulsion 50%) | 5.00 |
| Polyquaternium-11 | 1.00 |
| Dihydroxypropytrimonium Chloride | 1.00 |
| Water | Balance |

Example 7

A disposable, single use personal care towelette product is described according to the present invention. A 70/30 polyester/rayon non-woven towelette is prepared with a weight of 1.8 grams and dimensions of 15 cm by 20 cm. Onto this towelette is impregnated a composition with a quaternary ammonium salt as outlined in Table VII below.

TABLE VII

| INGREDIENT | WEIGHT % |
|---|---|
| Dihydroxypropytrimonium Chloride | 7.50 |
| Glycerin | 2.00 |
| Hexylene Glycol | 2.00 |
| Disodium Capryl Amphodiacetate | 1.00 |
| Gluconolactone | 0.90 |
| Silicone Microemulsion | 0.85 |
| Witch Hazel | 0.50 |
| PEG-40 Hydrogenated Castor Oil | 0.50 |
| Fragrance | 0.20 |
| Vitamin E Acetate | 0.001 |
| Water | Balance |

Example 8

A toilette bar illustrative of the present invention is outlined under Table VIII.

TABLE VIII

| INGREDIENT | WEIGHT % |
|---|---|
| Sodium Soap (85/15 Tallow/Coconut) | 77.77 |
| Dihydroxypropytrimonium Chloride | 3.50 |
| Glycerin | 2.50 |
| Sodium Chloride | 0.77 |
| Titanium Dioxide | 0.40 |
| Fragrance | 1.50 |
| Disodium EDTA | 0.02 |
| Sodium Etidronate | 0.02 |
| Fluorescer | 0.024 |
| Water | Balance |

Example 9

A shampoo composition useful in the context of the present invention is described in Table IX below.

TABLE IX

| Ingredient | Weight % |
|---|---|
| Ammonium Laureth Sulfate | 12.00 |
| Ammonium Lauryl Sulfate | 2.00 |
| Cocoamidopropyl Betaine | 2.00 |
| Sodium Lauroamphoacetate | 2.00 |
| Dihydroxypropytrimonium Chloride | 5.50 |
| Ethylene Glycol Distearate | 1.50 |
| Cocomonoethanolamide | 0.80 |
| Cetyl Alcohol | 0.60 |
| Polyquaternium-10 | 0.50 |
| Dimethicone | 1.00 |
| Zinc Pyridinethione | 1.00 |
| Sodium Citrate | 0.40 |
| Citric Acid | 0.39 |
| Sodium Xylene Sulfonate | 1.00 |
| Fragrance | 0.40 |
| Sodium Benzoate | 0.25 |
| Kathon CG ® | 0.0008 |
| Benzyl Alcohol | 0.0225 |
| Water | Balance |

Example 10

This Example illustrates an antiperspirant/deodorant formula incorporating the moisturizing actives according to the present invention.

TABLE X

| Ingredient | Weight % |
|---|---|
| Cyclopentasiloxane | 44 |
| Dimethicone | 20 |
| Aluminum Zirconium Trichlorohydrex Glycinate | 15 |
| Dihydroxypropytrimonium Chloride | 5.0 |
| $C_{18}$-$C_{36}$ Acid Triglyceride | 5.0 |
| Microcrystalline Wax | 3.0 |
| Glycerin | 3.0 |
| Silica | 2.5 |
| Dimethicone Crosspolymer | 1.0 |
| Fragrance | 0.5 |
| Disodium EDTA | 0.4 |
| Butylated Hydroxytoluene | 0.3 |
| Citric Acid | 0.3 |

Example 11

A toothpaste according to the present invention can be formulated with the ingredients listed under Table XI.

TABLE XI

| Ingredients | Weight % |
|---|---|
| Zeodent 115 ® | 20.00 |
| Glycerin | 18.00 |
| Xanthan Gum | 7.00 |
| Sodium Carboxymethyl Cellulose | 0.50 |
| Sodium Bicarbonate | 2.50 |
| Dihydroxypropytrimonium Chloride | 2.00 |
| Sodium Laurylsulfate | 1.50 |
| Sodium Fluoride | 1.10 |
| Sodium Saccharin | 0.40 |
| Titanium Dioxide | 1.00 |
| Pluronic F-127 ® | 2.00 |
| FD&C Blue No. 1 | 3.30 |
| Menthol | 0.80 |
| Potassium Nitrate | 5.00 |
| Water | balance |

Example 12

This Example provides the results of moisturization efficacy tests. These tests involved evaluation on Porcine epidermis utilized as a human skin model. Equipment and protocol are outlined below.

An environmental microbalance (Model MB-300W, VTI Corp., 2708 W 84th Street, Hialeah, Fla. 33016) was programmed to measure the change in weight of porcine skin as a function of relative humidity at a constant temperature and air flow. The porcine skin was evaluated before and after treatment with aqueous solutions of humectants to determine adsorption and retention of moisture.

Sample preparation was done as follows:
Epidermal sections of porcine skin were cut to approximately 4 cm×1 cm.
The skin was washed in a 10% detergent solution and dried in a dessicator to a constant weight. This represents the Untreated material.
The skin was soaked in a 1% by weight aqueous solution of the test sample for 15 minutes, excess fluid was blotted off and the skin was dried to constant weight in a dessicator. This represents the Treated material.

Sequence of conditions for the microbalance was as follows:
30 minutes at 0% relative humidity. (Insures that sample is dry.)
90 minutes at 80% relative humidity. (Determines amount of water picked up.)
90 minutes at 20% relative humidity. (Determines amount of water retained.)

The experiments were conducted as follows:
The weight of a piece of untreated skin was recorded continuously during the sequence.
The piece of untreated skin was treated with the test sample.
The weight of the treated piece of skin was recorded continuously during the sequence.
Data reduction consisted of calculating the percent weight change from the initial weight for the untreated and treated pieces of skin.
The reported data was the difference between each treated piece and its corresponding untreated piece. Results are recorded in Table XII.

TABLE XII

| Sample* | From 0 through 80% Relative Humidity | From 0 to 80 to 20% Relative Humidity |
|---|---|---|
| Dihydroxypropyl trimonium Chloride | 2.20 | 3.50 |
| Honeyquat ® | 0.31 | 0.70 |
| Honey | 0.24 | 0.02 |
| Quat ® 188 | 0.21 | 0.10 |
| Glycerin | 0.21 | 0.10 |

*All samples tested at 1% active material in water solution. Data points represent the difference in weight of treated skin minus untreated skin.

Evident from the results is that dihydroxypropyl trimonium chloride was not only effective for moisturizing at relatively high humidity but also exceptional at relatively low humidity. This contrasts with Quat® 188 (chlorohydroxypropyl trimonium chloride) which hardly showed any moisturization activity. These results were especially significant relative to glycerin which is normally used for moisturization purposes in cosmetic formulations.

Example 13

This Example details the synthesis of 2,3-dihydroxypropyl trimethylammonium chloride (identified in Table XII as dihydroxypropyl trimonium chloride). A 125 ml erlenmeyer flask was charged with 16.7 ml (53 mmol) of 3-chloro-2-hydroxypropyl trimethylammonium chloride (employed as a 60% material in water as Quat 188®). The flask was equipped with a dropping funnel and stirring bar. A solution of sodium hydroxide (55 ml, 55.0 mmol) was charged into the flask via the dropping funnel at a rate to maintain room temperature of the reaction. Once addition was complete, the solution was stirred under ambient conditions for about 12 hours, followed by heating at 50° C. for two hours.

Progress of the reaction was monitored by thin layer chromatography (TLC). Product was spotted on a 2.5 by 7.6 cm silica gel plate alongside the starting material and eluted with butanol:acetic acid:water (4:2:2) for approximately 50 minutes. Visualization was executed with ninhydrin stain and scorching on a hotplate.

Crude product solution was first acidified to pH of 7, and then concentrated to remove water. Ethanol (200 ml) was added to the crude product with stirring. Upon sitting, sodium chloride precipitated and was filtered off under vacuum. The filtrate was concentrated under vacuum on a Rotavap®, followed by additional drying under high vacuum (0.05 mmHg). A cloudy gel was obtained yielding the final product in 97% yield. TLC analysis indicated a major spot at $R_f$=0.27.

A 60 MHz proton NMR ($D_2O$ w/TSP) was run on the final product. The spectra confirmed the final product structure. Mass Spectrum analysis in positive ion mode revealed a $M^+$ of 134 (minus chlorine).

What is claimed is:

1. A method for moisturizing hands comprising topically applying to the hands of a person suffering from dry skin condition at 20% or less relative humidity a personal care composition comprising from about 0.1 to about 30% by weight of dihydroxypropyltri($C_1$-$C_3$ alkyl)ammonium salt in a cosmetically acceptable carrier.

2. The method according to claim 1 wherein the salt is present in an amount from about 1.5 to about 12% by weight of the composition.

3. The method according to claim 1 wherein the salt is dihydroxypropyltrimonium chloride.

4. The method according to claim 1 wherein the salt is present in an amount from 1.5 to about 12% by weight of the composition.

5. The method according to claim 1 wherein the composition is a leave-on skin lotion or cream.

6. A method for moisturizing human skin body parts comprising topically applying to the human skin body parts of a person suffering from dry skin under conditions of 20% or less relative humidity a personal care composition comprising from 1.5 to about 12% by weight of dihydroxypropyltri($C_1$-$C_3$ alkyl)ammonium salt in a cosmetically acceptable carrier and thereby imparting moisturization to the human skin body parts.

7. The method according to claim 6 wherein the salt is dihydroxypropyl trimonium chloride.

* * * * *